US008754657B2

(12) United States Patent
Capone

(10) Patent No.: US 8,754,657 B2
(45) Date of Patent: Jun. 17, 2014

(54) DETERMINATION OF WATER CUT AND SALINITY USING A COINCIDENCE FUNCTION

(75) Inventor: Enrique Osvaldo Capone, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 236 days.

(21) Appl. No.: 13/274,149

(22) Filed: Oct. 14, 2011

(65) Prior Publication Data

US 2012/0092024 A1 Apr. 19, 2012

Related U.S. Application Data

(60) Provisional application No. 61/455,282, filed on Oct. 18, 2010.

(51) Int. Cl.
*G01R 27/04* (2006.01)
(52) U.S. Cl.
USPC .......................................................... 324/640
(58) Field of Classification Search
USPC .......................................................... 324/640
See application file for complete search history.

(56) References Cited

U.S. PATENT DOCUMENTS

| 4,508,169 | A  | * | 4/1985  | Mut et al. ................ 166/250.01 |
|-----------|----|---|---------|---------------------------------------|
| 5,025,222 | A  | * | 6/1991  | Scott et al. ..................... 324/639 |
| 8,076,950 | B2 | * | 12/2011 | Wee .............................. 324/722 |
| 2005/0264302 | A1 | * | 12/2005 | Mohajer et al. ............... 324/639 |
| 2007/0239402 | A1 | * | 10/2007 | Scott ............................. 702/189 |
| 2008/0015792 | A1 | * | 1/2008  | Scott ............................... 702/25 |
| 2009/0093345 | A1 | * | 4/2009  | Findeisen ....................... 482/47 |
| 2009/0256579 | A1 | * | 10/2009 | Scott ............................. 324/643 |
| 2013/0153440 | A9 | * | 6/2013  | Kanzius ........................ 205/687 |

* cited by examiner

*Primary Examiner* — Patrick Assouad
*Assistant Examiner* — Demetrius Pretlow

(57) ABSTRACT

A salinity determining system for determining a salinity of water in a hydrocarbon emulsion of oil and water. The salinity determining system includes an antenna element in contact with the hydrocarbon emulsion and a switch coupled to the antenna element. The salinity determining system includes a first analyzer device configured to be coupled to the antenna element via the switch. The first analyzer device is associated with a first coincidence function based on first measured electrical parameters of transmitted radio-frequency (RF) energy. The salinity determining system also includes a second analyzer device configured to be coupled to the antenna element via the switch.

15 Claims, 5 Drawing Sheets

DETERMINATION OF WATER CUT AND SALINITY USING A COINCIDENCE FUNCTION

CROSS-REFERENCE TO RELATED APPLICATION(S) AND CLAIM OF PRIORITY

The present application is related to U.S. Provisional Patent. No. 61/455,282, filed Oct. 18, 2010 and entitled "DETERMINATION OF WATER CUT AND SALINITY OR WATER CUT USING A COINCIDENCE FUNCTION". Provisional Patent No. 61/455,282 is hereby incorporated by reference into the present application as if fully set forth herein. The present application hereby claims priority under 35 U.S.C. §119(e) to U.S. Provisional Patent No. 61/455,282.

The present application is related to U.S. patent application Ser. No. 12/416,884, filed Apr. 1, 2009 and entitled "SELF-CHECKING ANALYZER METHOD AND SYSTEM USING FREQUENCY RESPONSE" and U.S. patent application Ser. No. 12/416,878, filed Apr. 1, 2009 and entitled "SELF-CHECKING ANALYZER METHOD AND SYSTEM USING REFLECTED POWER/INSERTION LOSS". Patent application Ser. Nos. 12/416,884 and 12/416,878 are hereby incorporated by reference into the present application as if fully set forth herein.

TECHNICAL FIELD OF THE INVENTION

This application relates generally to analyzer systems and, more specifically, to water analyzer systems and methods.

BACKGROUND OF THE INVENTION

When crude petroleum oil is pumped to the surface of the earth, producers often attempt to determine the water content of the oil because water can corrode pipes and damage downstream processing equipment. Furthermore, the water has no value relative to the oil and, in fact, can become a disposal or environmental problem when finally removed from the oil.

The accurate determination of the water content and the validation of the amount of water in crude petroleum oil is particularly important during the sale and taxation of crude petroleum oil. The owner or seller of the oil does not want to pay taxes on water and the customer does not want to pay the price of oil for water. Such determinations and validations can be conducted online and offline during petroleum processing.

Offline methods involve physically sampling the stream and analyzing it in a laboratory setting. In the petroleum industry, sampling is usually done using a composite sampler, which automatically opens a sample valve attached to a pipeline at a certain time interval to collect an aggregate sample into a sample container. The objective is to collect a representative sample of the entire lot of petroleum under consideration. After collection, the composite sample is usually taken to a laboratory. The composite sample is then divided into aliquots, or sub-divisions of the composite sample, according to the various characterizations or analysis methods being implemented.

However, composite petroleum samplers and the associated analytical methods have problems and disadvantages, such as meeting a desired accuracy for a given determination. For example, results for composite samplers are typically only available at the end of a batch or a test, and there is no recourse if something goes wrong with the sampling system during the sampling process. At the end of the sampling and analysis, only a single number is available to consider. Additionally, the exposure of personnel to hazardous liquids associated with processing the samples is undesirable. Thus, the petroleum industry has continued to seek other methods that provide the required accuracy, speed, and safety.

Accordingly, the use of rapid on-line instruments such as densitometers, capacitance probes, radio-frequency (RF) probes, and microwave analyzers to measure the water content of petroleum products is becoming more common. In addition to providing increasingly accurate determinations of water content, real-time water content measured by on-line methods provides beneficial operational advantages. Knowledge of when water becomes present in petroleum as it is being produced and the quantity of the water provides an opportunity to remove the water before it corrodes or damages a transport pipeline, storage vessel, or shipping tanker.

Additionally, real-time data may show if the water is detected in several short periods of time or if it is present across the entire load of the petroleum. The results from real-time analyzers may be used as a comparison to the results from composite samplers. On-line measurement of, for example, physical and electrical properties via instrumentation reduces the need for human involvement in the process of characterizing a multiphase fluid mixture.

However, the calibration of on-line analyzers is extremely important. It is particularly important to determine the water cut (i.e., water percentage) and the water salinity as accurately as possible during the calibration procedure. Therefore, there is a need in the art for improved apparatuses and methods for accurately determining the water cut and salinity when calibrating and online analyzer.

SUMMARY OF THE INVENTION

A salinity determining system for determining a salinity of water in a hydrocarbon emulsion of oil and water is provided. The salinity determining system comprises an antenna element in contact with the hydrocarbon emulsion and a switch coupled to the antenna element. The salinity determining system further comprises a first analyzer device configured to be coupled to the antenna element via the switch, wherein the first analyzer device is associated with a first coincidence function based on first measured electrical parameters of transmitted radio-frequency (RF) energy in the hydrocarbon emulsion. The salinity determining system also comprises a second analyzer device configured to be coupled to the antenna element via the switch, wherein the second analyzer device is associated with a second coincidence function based on second measured electrical parameters of transmitted radio-frequency (RF) energy in the hydrocarbon emulsion. The salinity determining system is configured to determine an intersection point of the first and second coincidence functions and to use the intersection point to determine a salinity of water in the hydrocarbon emulsion.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

Figure 1:
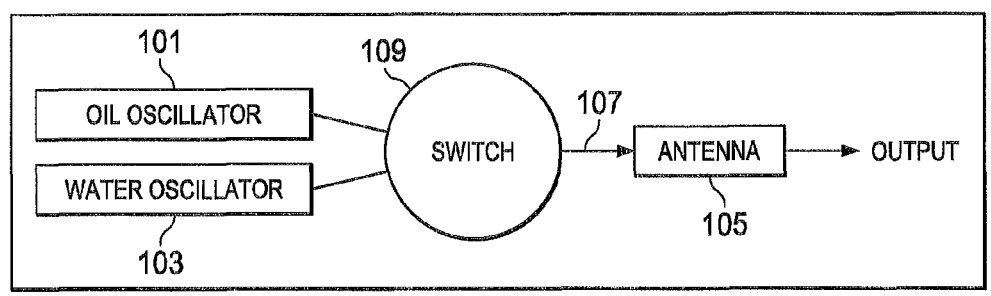
FIG. 1 illustrates analyzing circuitry having two measurement systems that are independent of one another.

FIGS. 1 through 6, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged analyzer system.

Given two independent microwave-based water cut measurements that have independent polynomial functions, the water cut (i.e., water percentage) and salinity of a hydrocarbon emulsion may be determined by finding the single point where the two functions intercept.

For a given emulsion, two independent analyzers have two different coincidence functions based on electrical measurement of transmitted energy. These functions are Function_1 (or F1) and Function_2 (or F2). In the equations below, MEP means "measured electrical parameters" and WC means "water cut". Coincidence Function_1 is defined in Equation 1 below:

$$WC1 = F1\{Salinity1, MEP1\}. \quad [\text{Eqn. 1}]$$

Coincidence Function_2 is defined in Equation 2 below:

$$WC2 = F2\{Salinity2, MEP2\}. \quad [\text{Eqn. 2}]$$

For a given emulsion, the two independent analyzers are exposed to the same fluids at the same time. In this case, WC1 and WC2 are identical. Salinity1 and Salinity2 are also identical. For that reason, Equation 1 may be made equal to Equation 2 and solved for salinity as shown in Equations 3 and 4 below:

$$WC1 = W2 = \text{Current WC}, \quad [\text{Eqn. 3}]$$

and $$\text{Salinity1} = \text{Salinty2} = \text{Current Salinity}. \quad [\text{Eqn. 4}]$$

The first measured electrical parameters (MEP1) are different from the second measured electrical parameters (MEP2) because of the independent polynomial functions of both analyzers.

In particular embodiments, the relationship between functions F1 and F2 may be expressed as shown in Equation 5 below:

$$F1\{\text{Current Salinity}, MEP1\} = F2\{\text{Current Salinity}, MEP\_2\}. \quad [\text{Eqn. 5}]$$

Equation 5 can be easily solved for Current Salinity. After the Current Salinity is determined, the Current Water Cut can be calculated using Equation 1 or Equation 2.

The two coincidence functions may be obtained by connecting the same probe to two different electronics with inherently different functions in the same enclosure.

The independent functions of salinity and water percentage have different frequencies and slopes of the polynomial function defined by calibration during manufacturing of the analyzer.

The present disclosure provides an automatic salinity determining analyzer system. The analyzer system includes a pipeline for receiving a multi-phase fluid flow and a first measuring device configured to provide a first frequency response corresponding to the multi-phase fluid flow. The analyzer system also includes a second measuring device differing in frequency response from the first measuring device and configured to provide a second frequency response corresponding to the multi-phase fluid flow.

In particular embodiments of the system, a switch is configured to connect the first measuring device to an antenna element to obtain the first frequency response and to connect a second measuring device to the antenna element to obtain the second frequency response. The second measuring device can be a second oscillator. The second oscillator or a third oscillator may be one of two physical oscillators connected by the switch, but with a third frequency selected by a voltage variable capacitor (varactor) within the same oscillator circuit. This third frequency provides curves that are independent from the second frequency due to dispersion or the like, which affects the measured variables versus frequency.

FIG. 1 illustrates exemplary analyzing circuitry 100 according to this disclosure. The embodiment of analyzing circuitry 100 shown in FIG. 1 is for illustration only. Other embodiments of analyzing circuitry 100 may be used without departing from the scope of this disclosure.

Analyzing circuitry 100 comprises two measurement systems that are independent of one another according to the principles of this disclosure. To alert a user that an analyzing system is not operating within calibrated values or that a failure has occurred, analyzing circuitry 100 performs real-time checking of the salinity by using two measurement systems that are independent of one another. In this particular embodiment, the two measurement systems take the form of oil oscillator 101 and water oscillator 103. Oil oscillator 101 and water oscillator 103 are independent of one another in terms of their tuning elements, active devices, and/or matching circuitry.

According to the principles of the present disclosure, Oil oscillator 101 provides a first frequency output and water oscillator 103 provides a second frequency output. However, due to the use of a varactor in water oscillator 103, water oscillator 103 is further capable of providing a third frequency output that is selected by the varactor.

In FIG. 1, oil oscillator 101 and water oscillator 103 both feed coaxial antenna 105 via coaxial line 107. Oil oscillator 101 and water oscillator 103 are used to match energy into two emulsion types: 1) a water-in-oil emulsion and 2) an oil-in-water emulsion. In a water-in-oil emulsion, the oil surrounds the water like an insulator, resulting in the properties of a capacitive load. In an oil-in-water emulsion, the water surrounds the oil and is conductive, resulting in the properties of a resistive load.

As noted, in a water-in-oil emulsion, the oil surrounds the water as an emulsion and is insulating. In some embodiments, this emulsion is perceived as a 50 ohm load in line 107 at the beginning and decreases in impedance as the percentage of water increases in the emulsion. Solid state switch 109 is used to isolate one oscillator while connecting the other oscillator to coaxial antenna 105. Solid state switch 109 may be, for example, a radio frequency (RF) switch.

Figure 2:
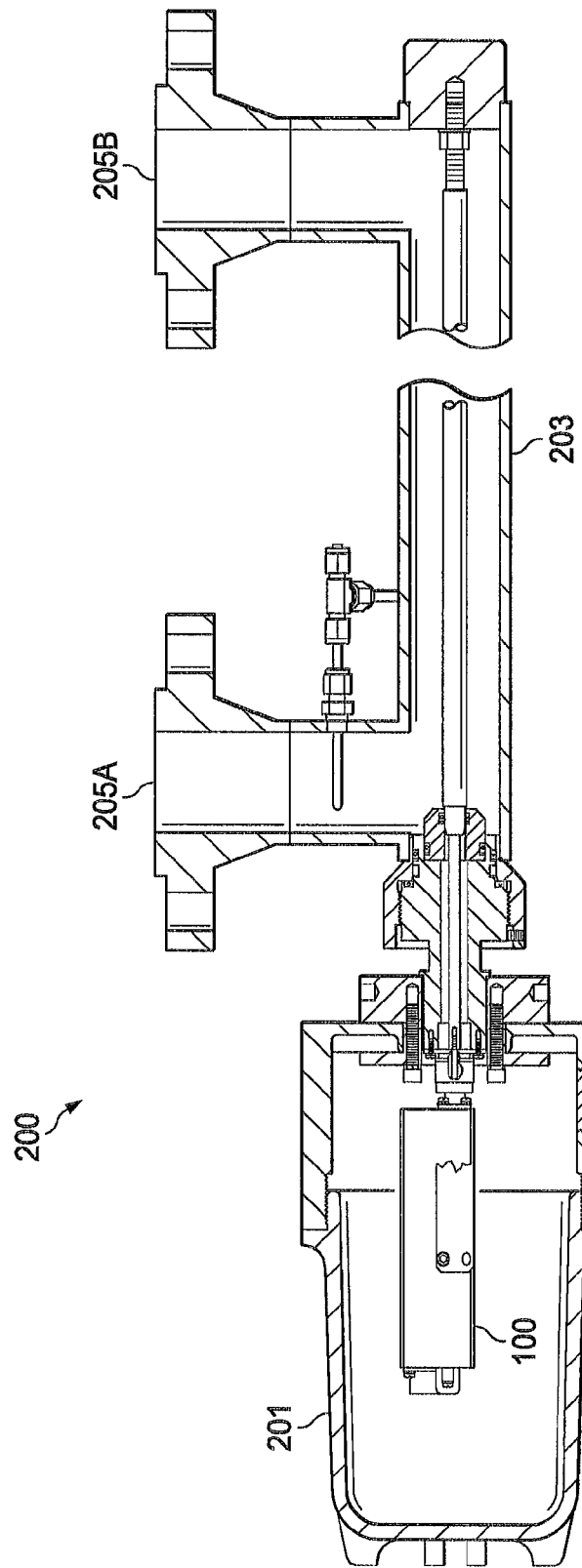
FIG. 2 illustrates a self-checking analyzer system having analyzing circuitry according to an embodiment of the disclosure.

FIG. 2 illustrates exemplary self-checking analyzer system 200 according to this disclosure. The embodiment of self-checking analyzer system 200 shown in FIG. 2 is for illustration only. Other embodiments of self-checking analyzer system 200 could be used without departing from the scope of this disclosure.

Self-checking analyzer system 200 comprises analyzing circuitry 100 according to an embodiment of this disclosure. Self-checking analyzer system 200 includes measurement unit 201, which includes analyzing circuitry 100 described above. Measurement unit 201 is in contact with a multiphase fluid flowing through a pipeline 203. The measurement unit 201 is able to measure the frequency response and the reflected power/insertion loss of oil oscillator 101 and water oscillator 103 to the multiphase fluid as the multiphase fluid flows through pipeline 203. In this embodiment, the multiphase fluid enters and exits pipeline 203 via flanges 205A and 205E.

Figure 3:
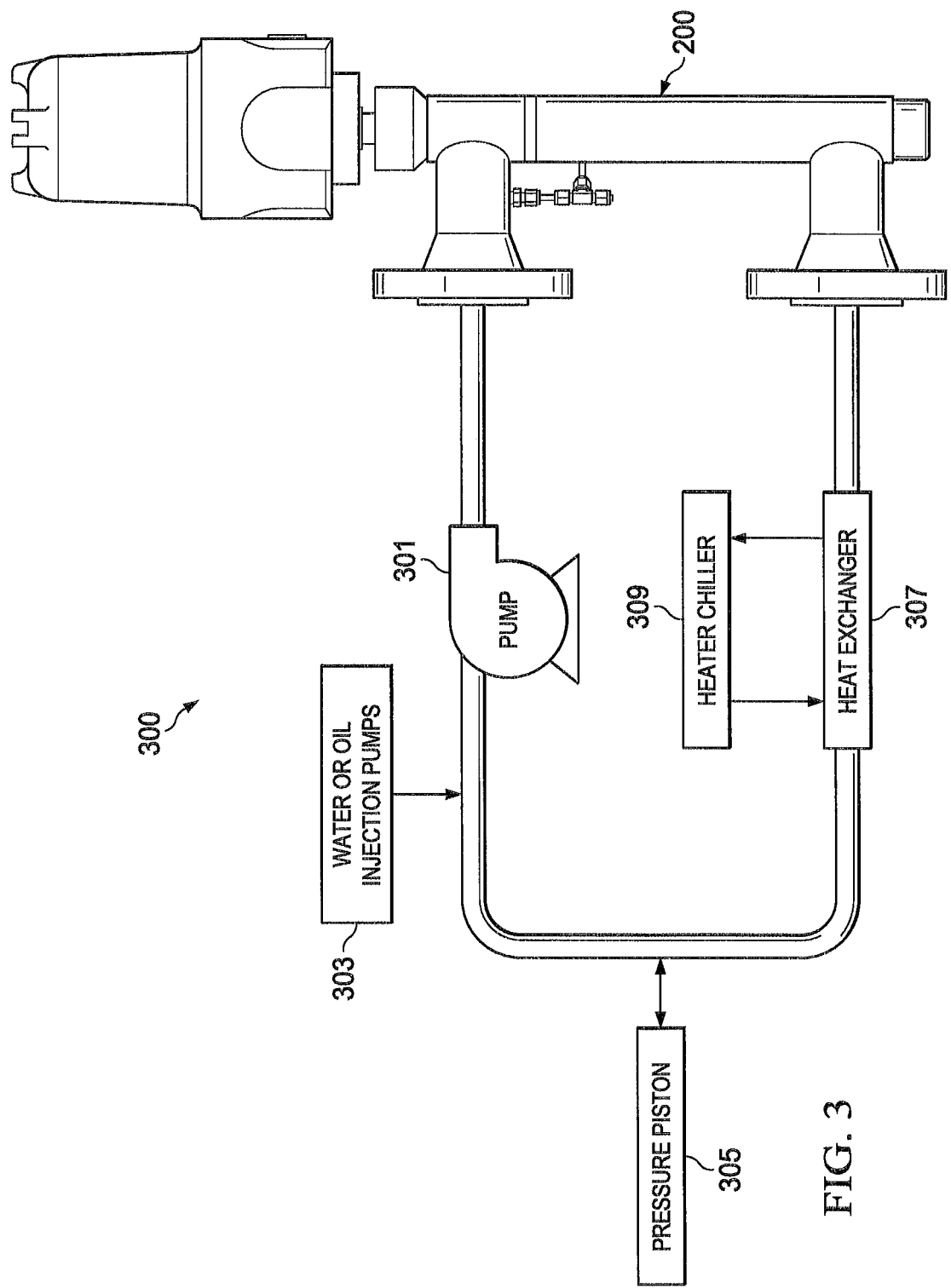
FIG. 3 illustrates a calibration flow loop for calibrating a self-checking analyzer system according to an embodiment of this disclosure.

FIG. 3 illustrates calibration flow loop 300 for calibrating self-checking analyzer system 200 according to an embodiment of this disclosure. In addition to self-checking analyzer system 200, calibration flow loop 300 includes pump 301 for pushing a multiphase fluid mixture through calibration flow loop 300. Calibration flow loop 300 further includes one or more water or oil injection pumps 303, pressure piston 305, and heat exchanger 307, which is in contact with heater/chiller 309.

Calibration flow loop 300 is loaded with 100% oil (or water) and then water (or oil) is injected into calibration flow loop 300 via injection pumps 303. The measurements taken as oil or water is injected into calibration flow loop 300 are used to generate calibration curves for oil oscillator 101 and the two water oscillators 103 (i.e. second frequency and third frequency) to indicate the frequency response and the reflected power/insertion loss of self-checking analyzer system 200 at various water percentages. According to the principles of the present disclosure, the two water oscillators 103 provide two coincidence functions needed for salinity determination and further water cut calculation.

Figure 4:
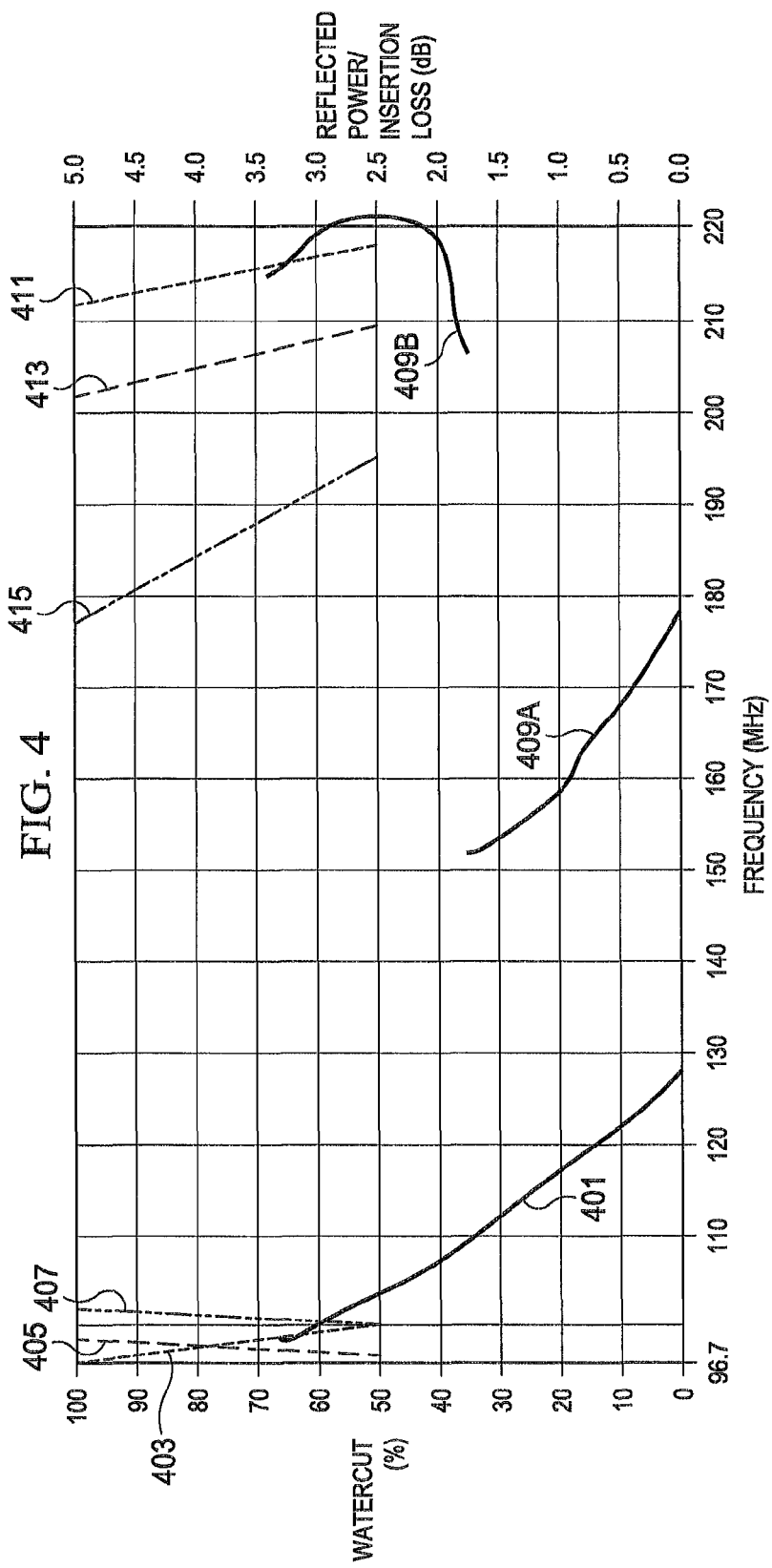
FIG. 4 illustrates an example of calibrations curves for an oil oscillator and a water oscillator according to an embodiment of this disclosure.

FIG. 4 illustrates an example of calibrations curves for oil oscillator 101 and water oscillator 103 according to an embodiment of this disclosure. The left side of FIG. 4 shows the calibration curves for oil oscillator 101, which range in frequency from 96.7 MHz to 128 MHz. The right side of FIG. 4 shows the calibration curves for water oscillator 103, which range in frequency from 152 MHz to 221.1 MHz.

With regard to the calibration curves for oil oscillator 101 on the left side of FIG. 4, oil emulsion curve 401 represents the calibration curve for oil oscillator 101. Because the water continuous phase (oil-in-water) is conductive due to the salinity of the water, a number of separate calibrations are made to obtain a family of salinity water emulsion curves 403, 405, and 407. For example, salt water emulsion curve 403 was obtained at 0.1% salt content, salt water emulsion curve 405 was obtained at 3% salt content, and salt water emulsion curve 407 was obtained at 11% salt content.

With regard to the calibration curves for water oscillator 103 on the right side of FIG. 4, oil emulsion curves 409A and 409B represent the oil emulsion for the water oscillator 103. Oil emulsion curve 409 is discontinuous in that at 32% water the frequency is 152 MHz and jumps to 209.2 MHz at 33% water. The reason for this jump is that the technology of load-pulled oscillators provides for the returning of the frequency to a rollover frequency upon transitioning through 180 degrees of phase shift. Because load-pulled oscillators designed and matched for the water phase are not normally used for the oil continuous emulsion phase, the discontinuity or jump in frequency does not interfere with measurements. Like oil oscillator 101 curves, water oscillator 103 curves also include, for example, salt water emulsion curve 411 obtained at 0.1% salt content, salt water emulsion curve 413 obtained at 3% salt content, and salt water emulsion curve 415 obtained at 11% salt content.

In one embodiment, validation of a measurement can be done simply by comparing the frequencies of oil oscillator 101 and water oscillator 103 with respect to the calibration curves corresponding to the same conditions of salinity and temperature. The frequencies for oil oscillator 101 and water oscillator 103 are independent of one another and the frequency response of each will be affected differently due to any events (for example, problems with the liquid seals at the antenna, a bad component, or changes in the internal reference voltages) that may require the system to be recalibrated.

Figure 5:
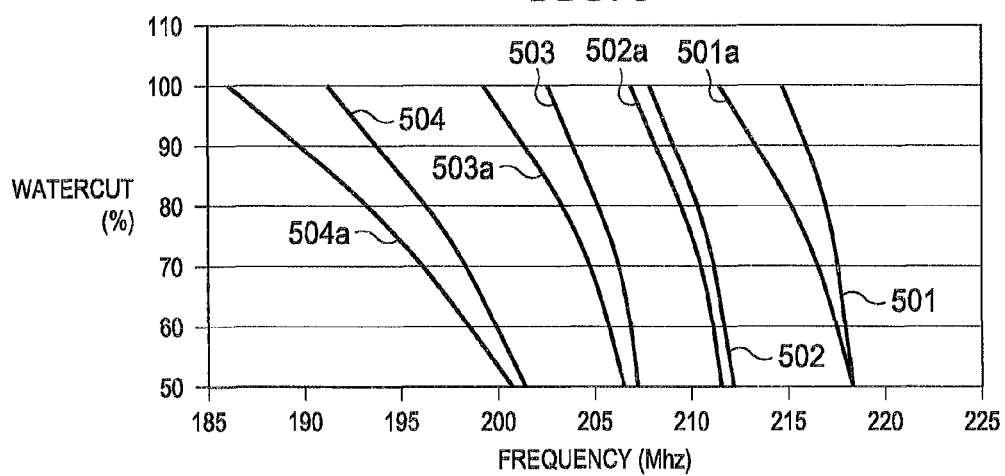
FIG. 5 illustrates calibration curves for a water oscillator according to an embodiment of this disclosure.

FIG. 5 illustrates calibration curves 501-504 and 501a-504a. The varactor enables water oscillator 103 to operate as two different oscillators, depending on the varactor capacitance setting. Calibrations curves 501, 502, 503 and 504 correspond to water oscillator 103 using the controllable varactor to select an independent second frequency response in water oscillator 103. Calibration curves 501a, 502a, 503a and 504a correspond to water oscillator 103 changing the varactor setting to move from the second frequency response to an independent third frequency response on the same water oscillator 103. FIG. 5 shows the calibration curves for 4 different salinities for each water oscillator setting.

Figure 6:
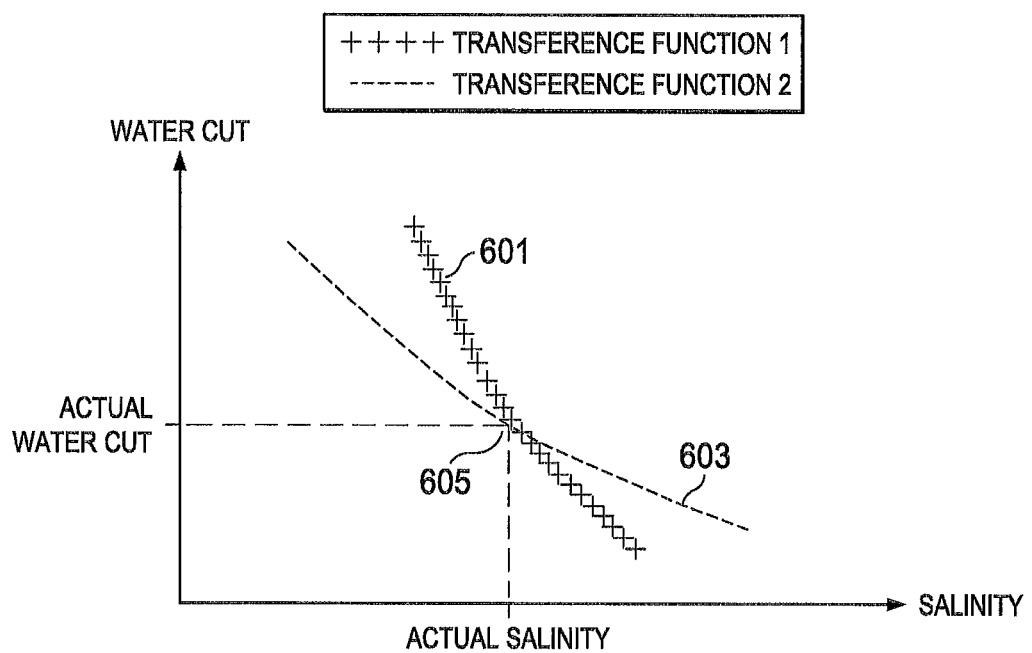
FIG. 6 illustrates two separate curves for the same salinity where a solution is described at a point where the two curves intersect according to an embodiment of this disclosure.

FIG. 6 illustrates two separate curves 601 and 603 for the same salinity, where the solution is described at intersection point 605 where curves 601 and 603 intersect. As noted above, given two independent microwave-based water cut measurements that have independent polynomial functions, the water cut and salinity of a hydrocarbon emulsion may be determined by finding the single point where the two functions intercept.

In particular, the two coincidence functions (or transfer functions) in FIG. 6 may be obtained by connecting the same probe to two different electronics with inherently different functions in the same enclosure. The two coincidence functions in FIG. 6 correspond to Equations 1 and 2 above. The independent functions of salinity and water percentage have different frequencies and slopes of the polynomial function defined by calibration during manufacturing of the analyzer.

Thus, by operating water oscillator 103 at two different varactor settings, the frequency responses may be used to determine curves 601 and 603 in FIG. 6. Water oscillator 103 is used because the frequency response is more sensitive that oil oscillatory 101. The intersection point 605 of curves 601 and 603 provides an accurate determination of both water cut and salinity during calibration.

It is advantageous to set definitions of certain words and phrases used in this document. The term "couple" and its derivatives refer to any direct or indirect communication between two or more elements, whether or not those elements are in physical contact with one another. The terms "include" and "comprise," as well as derivatives, mean inclusion without limitation. The term "or" is inclusive, meaning and/or. The phrases "associated with" and "associated therewith," as well as derivatives, may mean to include, be included within, interconnect with, contain, be contained within, connect to, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure as defined by the claims.

What is claimed is:

1. A salinity determining system for determining a salinity of water in a hydrocarbon emulsion of oil and water, the salinity determining system comprising:
    an antenna element configured to be in contact with the hydrocarbon emulsion;
    a switch coupled to the antenna element;
    a first analyzer device configured to be coupled to the antenna element via the switch, wherein the first analyzer device is associated with a first coincidence function based on first measured electrical parameters of transmitted radio-frequency (RF) energy in the hydrocarbon emulsion; and
    a second analyzer device configured to be coupled to the antenna element via the switch, wherein the second analyzer device is associated with a second coincidence function based on second measured electrical parameters of transmitted radio-frequency (RF) energy in the hydrocarbon emulsion,
    wherein the salinity determining system is configured to determine an intersection point of the first and second coincidence functions and to use the intersection point to determine a salinity of water in the hydrocarbon emulsion.

2. The salinity determining system of claim 1, wherein the first analyzer device and the second analyzer device comprise a water oscillator having a varactor that may be configured to operate at a first frequency response associated with the first analyzer device and to operate at a second frequency response associated with the second analyzer device.

3. The salinity determining system of claim 1, wherein the salinity determining system is further configured to use the intersection point to determine a water cut of the hydrocarbon emulsion.

4. The salinity determining system of claim 1, further comprising a third analyzer device configured to be coupled to the antenna element via the switch, wherein the third analyzer device is associated with a third coincidence function based on third measured electrical parameters of transmitted radio-frequency (RF) energy in the hydrocarbon emulsion.

5. The salinity determining system of claim 4, wherein the third analyzer device comprises an oil oscillator.

6. A multi-phase fluid analyzer system comprising:
    a pipeline for receiving a multi-phase fluid flow;
    an antenna element coupled to the pipeline and in contact with the multi-phase fluid flow;
    a switch coupled to the antenna element; and
    a salinity determining system comprising:
        a first analyzer device configured to be coupled to the antenna element via the switch, wherein the first analyzer device is associated with a first coincidence function based on first measured electrical parameters of transmitted radio-frequency (RF) energy in the multi-phase fluid flow; and
        a second analyzer device configured to be coupled to the antenna element via the switch, wherein the second analyzer device is associated with a second coincidence function based on second measured electrical parameters of transmitted radio-frequency (RF) energy in the multi-phase fluid flow,
    wherein the salinity determining system is configured to determine an intersection point of the first and second coincidence functions and to use the intersection point to determine a salinity of water in the multi-phase fluid flow.

7. The multi-phase fluid analyzer system of claim 6, wherein the first analyzer device and the second analyzer device comprise a water oscillator having a varactor that may be configured to operate at a first frequency response associated with the first analyzer device and to operate at a second frequency response associated with the second analyzer device.

8. The multi-phase fluid analyzer system of claim 6, wherein the salinity determining system is further configured to use the intersection point to determine a water cut of the multi-phase fluid flow.

9. The multi-phase fluid analyzer system of claim 6, further comprising a third analyzer device configured to be coupled to the antenna element via the switch, wherein the third analyzer device is associated with a third coincidence function based on third measured electrical parameters of transmitted radio-frequency (RF) energy in the multi-phase fluid flow.

10. The multi-phase fluid analyzer system of claim 4, wherein the third analyzer device comprises an oil oscillator.

11. A method of determining a salinity of water in a hydrocarbon emulsion of oil and water, the method comprising:
    coupling a first analyzer device to an antenna element in contact with the hydrocarbon emulsion;
    determining a first coincidence function associated with the first analyzer device, the first coincidence function based on first measured electrical parameters of transmitted radio-frequency (RF) energy in the hydrocarbon emulsion;
    coupling a second analyzer device to the antenna element in contact with the hydrocarbon emulsion;
    determining a second coincidence function associated with the second analyzer device, the second coincidence function based on second measured electrical parameters of transmitted radio-frequency (RF) energy in the hydrocarbon emulsion;
    determining an intersection point of the first and second coincidence functions; and
    determining a salinity of water in the hydrocarbon emulsion based on the intersection point.

12. The method of claim 11, wherein the first analyzer device and the second analyzer device comprise a water oscillator having a varactor that may be configured to operate at a first frequency response associated with the first analyzer device and to operate at a second frequency response associated with the second analyzer device.

13. The method of claim 11, further comprising determining a water cut of the hydrocarbon emulsion based on the intersection point.

14. The method of claim 11, further comprising coupling a third analyzer device to the antenna element in contact with the hydrocarbon emulsion, wherein the third analyzer device is associated with a third coincidence function based on third measured electrical parameters of transmitted radio-frequency (RF) energy in the hydrocarbon emulsion.

15. The method of claim 14, wherein the third analyzer device comprises an oil oscillator.

* * * * *